(12) United States Patent
Paris

(10) Patent No.: US 8,734,839 B2
(45) Date of Patent: May 27, 2014

(54) LIQUID COMPOSITIONS FOR SOFT SUSTAINED-RELEASE CAPSULES AND METHOD FOR PRODUCTION

(76) Inventor: Laurence Paris, Commentry (FR)

( * ) Notice: Subject to any disclaimer, the term of this patent is extended or adjusted under 35 U.S.C. 154(b) by 2024 days.

(21) Appl. No.: 10/511,260

(22) PCT Filed: Apr. 15, 2003

(86) PCT No.: PCT/FR03/01195
§ 371 (c)(1),
(2), (4) Date: Jun. 20, 2005

(87) PCT Pub. No.: WO03/086368
PCT Pub. Date: Oct. 23, 2003

(65) Prior Publication Data
US 2005/0244489 A1     Nov. 3, 2005

(30) Foreign Application Priority Data

Apr. 15, 2002 (FR) ..................... 02 04697

(51) Int. Cl.
*A61K 9/48* (2006.01)
(52) U.S. Cl.
USPC ........................................................ 424/451
(58) Field of Classification Search
USPC ........................................................ 424/451
See application file for complete search history.

(56) References Cited

U.S. PATENT DOCUMENTS

| | | | |
|---|---|---|---|
| 6,346,239 B1 * | 2/2002 | Mallo et al. ............... | 424/70.16 |
| 6,355,272 B1 * | 3/2002 | Caramella et al. ........... | 424/489 |
| 6,375,959 B1 * | 4/2002 | Mallo et al. .................. | 424/401 |
| 6,503,955 B1 * | 1/2003 | Dobrozsi et al. ............ | 514/772.4 |
| 2001/0051686 A1 | 12/2001 | Tabacchi et al. | |
| 2001/0053801 A1 | 12/2001 | Tabacchi et al. | |
| 2002/0032243 A1 | 3/2002 | Tabacchi et al. | |

FOREIGN PATENT DOCUMENTS

| | | |
|---|---|---|
| EP | 0095123 A2 | 11/1983 |
| EP | 0173293 A2 | 3/1986 |
| FR | 2774907 | 8/1999 |
| JP | 63-246332 | 10/1988 |
| JP | 63-246333 | 10/1988 |
| WO | WO 9936445 | 7/1999 |
| WO | WO 9942521 | 8/1999 |
| WO | WO 0135922 | 5/2001 |

OTHER PUBLICATIONS

Cole et al, Enteric Coated HPMC Capsules Designed to Achieve Intestinal Targeting, International Journal of Pharmaceutics, vol. 231, Issue 1, Jan. 2002, p. 83-95.*
Ewart Cole, et al, Enteric Coated HPMC Capsules Designed to Achieve Intestinal Targeting, 231 Int. J Pharma. 83 (Jan. 2002).*
Patent Abstracts of Japan, Japanese Patent Pub. No. 63246322, Pub. Date Oct. 13, 1988.
Derwent Abstract, XP-002223635, published Oct. 13, 1988 for Japanese Patent Publication 63246333A.

* cited by examiner

*Primary Examiner* — Sean Basquill
(74) *Attorney, Agent, or Firm* — Paul & Paul

(57) ABSTRACT

The invention relates to liquid compositions for production of soft sustained-release capsules. According to the invention, the sustained release of the active agent is obtained by in situ formation of a matrix, more or less consolidated and biodegradable, by physical modification of the capsule contents on coming into contact with digestive juices on the opening thereof. The above leads to a release time of more than one hour for the active agent previously dissolved or dispersed by means of solvents, said release being modulated by addition of appropriate adjuncts. The invention further relates to a method for production of said liquid compositions. The above finds application in the pharmaceutical, cosmetic and dietary fields.

21 Claims, 2 Drawing Sheets

LIQUID COMPOSITIONS FOR SOFT SUSTAINED-RELEASE CAPSULES AND METHOD FOR PRODUCTION

FIELD OF APPLICATION OF THE INVENTION

This invention deals with the pharmaceutical, cosmetic, and dietetic fields and in particular with the field of systems with extended release of the active substances inside the human body.

DESCRIPTION OF PRIOR ART

Among the routes of administration of the active substances inside the human body, the oral administration represents the favorite way of administrating systems with extended release. Most of such systems are under a solid form. These are tablets and certain hard capsules containing micro-granules. Such forms sustained release or so-called programmed release are numerous and belong to various categories according to the excipients used to slow down the release of active substances. These are:

matrixforms:

hydrophilic matrices based on cellulose derivatives, starch derivatives and other polysaccharides endowed with swelling properties resulting in the formation of a viscous gangue when in contact with digestive secretions. In the present case, the release of the active substance is a function of:

the thickness of the viscous gangue,
the enzymes present in the digestive environment. In the case of hydrophilic matrices, amylases are very active on celluloses and starches
and an erosion phenomenon.

the inert matrices based on plastic material such as PVC, metacrylic resins ("Eudragit®"), carbomers ("Carbopol®"), etc. In the present case, the release of the active substance is made through:

a simple mechanism of solubilization/diffusion through canalicules
and by a progressive erosion phenomenon of the matrice.

mineral matrices based on phosphates of calcium, etc. The mechanism of the release of the active substance is identical to that of the inert matrices.

lipidic matrices based on glycerides (mono-, di-, and triglycerides), fatty acids and alcohols, various esters of fatty acids and alcohols with low molecular weight, waxes constituted mainly of esters of alcohols and of superior acids, etc. In the present case, the release of the active substance is a function of:

the fusion point of the fatty mass
the hydro-lipophilic balance (HLB) of the fatty mass
the digestive enzymes, such as the lipases present in the pancreatic juice
and the erosion phenomenon of the matrice. The fusion point of the mass, its HLB and the action of the digestive enzymes result in the fact that the release of the active substance from such matrice is being very difficult to master in vitro but also in vivo as the temperature of the human body as well as the production of the digestive enzymes lead to very important variations intra and inter individuals.

The micro-matrices or pellets based on the various constituents mentioned hereabove. The release of the active substance occurs in the same manner as in the various preceding cases.

the coated forms. Those are classic tablets and microgranules, which have been subjected to a coating of substances endowed with specific proprieties allowing a slow release through the formed membrane. The release may be either:

pH dependent. The coating is dissolved progressively according to the pH of the digestive tract. Generally, such substances are hardly soluble in an acid environment and become progressively soluble according to the pH of the digestive tract, from 1.2 (stomach) to 5.3 (proximal intestine), 6.8 (distal intestine) and 7.5 (big intestine). Generally, such coatings are made of metacrylic resins soluble at different pHs.

pH independent. The coating does not dissolve but becomes progressively porous according to the pH of the digestive tract. Such coatings based on metacrylic resins are ideally suited as no biological factor has an influence on their mechanical properties. Thus, we obtain osmotic membranes through which the dissolved active substance is diffused.

The second form of administration of active substances by oral administration is the liquid form. The latter comes as:

aqueous or hydro-alcoholic solutions or solutions containing solvents such as polyoxyethylene glycols, propylene glycol, etc.

aqueous or hydro-alcoholic solutions or solutions containing other solvents suitable on the toxicological level.

Such forms may be presented "in bulk", in bottles or in unitary doses, such as the soft capsules or the "Licaps®" hard capsules with a liquid content. Under such form, very few forms of extended release do exist because of the difficulty in avoiding the release of the active substance in situ during time.

Tests have been conducted by fixing the active substances on resins that exchange ions, such as resinates of codeine, of pholcodine, of phenyltoloxamine, etc. American U.S. Pat. No. 3,244,588 and British patent GB 10056458 of MPHILLER Nielson mention the preparation of such resins exchanging ions for antitussive medications. These complexes may thus be dispersed in a phase that does not allow the release of the active substance and may presented either under the form "in bulk" or under the form of soft capsules or of hard capsules.

Another European patent EP 0173293 of MERELL DOW mentions the preparation of a lipidic matrix based on solid paraffin and on polyethylene glycol for a conditioning in soft capsules.

The U.S. Pat. No. 57,776,482 and WO9501787 mention a sustained release system with extended release presented under the form of coated micro-granules dispersed in a classical oily phase. The specificity of such micro-granules is that they are coated in order to allow a progressive release in time of the active substance after the opening of the capsule and the dispersion of said micro-granules into the digestive secretions.

The U.S. Pat. No. 5,645,848 presents a sustained release system under the form of soft capsules for lens cleansing. The progressive release of the components is obtained through an enzymatic attack of the gelatine coating presenting a specific composition.

On the other hand, an important work has been conducted by NASHED Norman in his thesis at the Louis Pasteur University in Strasbourg in 1984-1985; with respect to sustained release soft capsules, using the work done on lipidic matrices ("Witepsol®", "Gelucire®", "Suppocire®", "Precirol®"), on some natural derivates showing a phenomenon of in situ precipitation at the contact of water (white lac and colophony), and on certain polymers such as silicones. In all cases, results turned negative because of a release that was either too fast or too slow and too difficult to master.

The too quick release in vivo was observed in the case of lipidic matrices and that despite results that were quite correct in vitro. Such difference is due to the action of the digestive enzymes, which was not taken into account during the in vitro trials. The only positive results were observed on soft capsules being one year old. A comparative study with the in vivo tests at T=0 shows that such type of soft capsules does not age well. Indeed, the fatty material used for the manufacturing of this type of capsule presents a polymorphism phenomenon that plays a major role on the melting point of the fatty mass. Therefore, a heating of the fatty mass may lead to a change that is not negligible of the biodisponibility of the active substance from such matrice. That phenomenon has been widely studied by MOES (A) (Pharma. Acta Helv., 1980, 55, 307-311) and (Sci. Tech. Pharm., 1980, 9, 263-288), LUTTON (E. S) (J. Am. Oil Chem. Soc., 1972, 49, 1) and BOYMOND C. and HANS J. B. (Bulletin de la Société de Pharmacie, Strasbourg, 1978, 22, 203-217).

A detailed study of all theses patents in the field of the soft capsule has not been able to bring to light any efficient solution that would allow us to obtain a sustained release soft.

BRIEF DESCRIPTION OF THE DRAWINGS

The features of the present invention will be apparent and understood from a reading of the following description of the invention with the accompanying drawings, in which.

DESCRIPTION OF THE INVENTION

Figure 1:
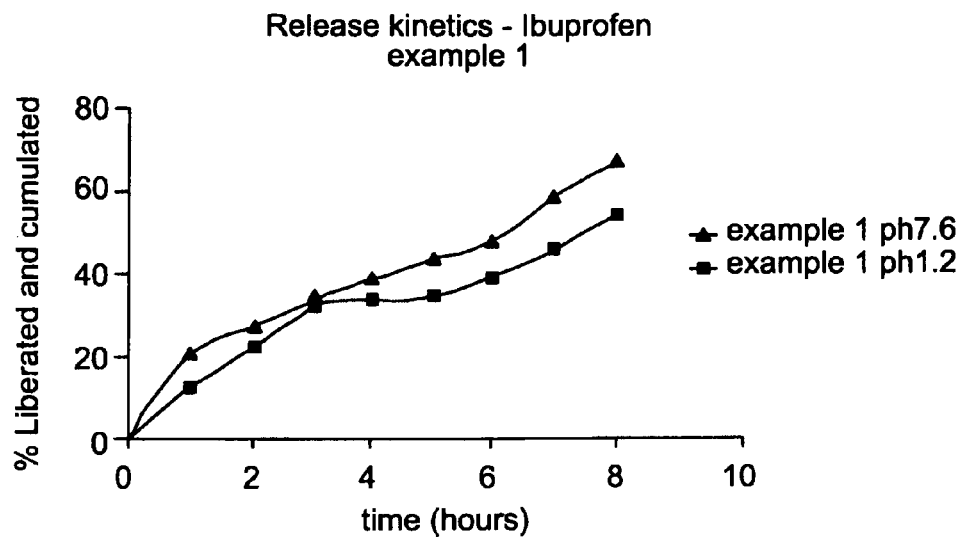
FIG. 1 is a graph of Example 1.

Taking stock of this situation and in order to find a remedy to such problem, the invention is proposing an original concept of liquid compositions intended for the preparation of sustained release capsules, remarkable in that the sustained release of the active substance is obtained through the in situ formation of a matrice that, being more or less compact and biodegradable, is obtained through the physical and instantaneous modification of the content of the capsule at the contact of the digestive secretions when it is opened, leading to a release during a period exceeding an hour of the active substance previously dissolved or dispersed by means of solvents, such release being modulable by the incorporation of appropriate additives.

Thus, the goal of this invention is to generate in situ, after the opening of the soft capsule or of the hard capsule "Licaps®", a matrice that may be biodegradable or not, from which the release of the active substance is, if possible, independent of the pH and/or dependent of the action of the digestive secretions depending on the excipients used in order to generate or reinforce the solidity of said matrice. The formation of the matrice in situ is such that said formation occurs almost instantaneously at the opening of the capsule, and which may be even initiated inside the soft capsule or hard capsule "Licaps®".

"Biodegradable" means the degradation of a support obtained by a biological mechanism, such as the action of enzymes but also by a mechanism of mechanical erosion due to the intestinal peristalsis.

"Initiated" means the apparition of a matrice outline inside the capsule before opening or dissolution of the coating of the latter.

This invention may be applied to soft capsules and hard capsules made of gelatine but also to soft capsules or hard capsules with a coating made with other materials, other than gelatine, such as caraghenanes, starches and their derivatives, hydroxypropylmethycelluloses and their derivatives, as well as polymers of polyvinyl alcohol.

This invention is based on the fact that some substances in the liquid state in solvents that are non toxic for the human organism, do jell or form a porous lattice very rapidly when put in contact with water or digestive secretions. Therefore, we obtain a viscous gangue or a poriferous structure from which the active substance is diffused progressively in time. Such substances being mainly synthetic material, which is highly used in the pharmaceutical and cosmetic fields, the release of the active substance is very little pH dependent, but mostly such release is not or very slightly influenced by the digestive enzymes because of the protection brought by the viscous gangue for the additives likely to be added in order to modulate the release of the active substance during time.

"To jell" means broadly either the thickening of a liquid mass, or the obtention of a solid and flexible mass, such as it has been observed with gelatine.

"Rapidly" means preferentially the instantaneous modification of the content after the opening of the capsule, in a time frame comprised between the second and 10 minutes. In order to obtain said matrices, being the object of this invention, we need to call upon substances being called matricial substances that, by gelification and/or by the formation of a porous lattice and with contact with water or with digestive secretions, have the power to undergo a physical transformation almost instantaneously. Such substances may be used alone and may give birth to a viscous gangue or to a poriferous structure, in which the active substance(s) are dissolved or dispersed. The same substances may be used in association with other excipients in order to reinforce the structure of said matrice. In association with other excipients, such matricial substances serve as "bonding material".

"Bonding material" means substances acting as cement between the particles of a lattice in order to reinforce a structure that is more or less strong.

Thus, such matricial substances avoid the dispersion of other excipients inside the digestive secretions by entrapping them inside the viscous gangue or the poriferous structure. Such entrapping is leading either to a progressive swelling or to the precipitation of the excipients inside the said viscous matrice. Therefore, depending on the solidity of the obtained matrice, the release of the active substance included in such a system may vary between one and twenty-four hours. The matricial substances allowing the formation of said matrices and serving as "bonding material" belong to two classes of products:

the inverted latexes
the lipophilic hydrocolloide solutions.

The inverted latexes are compositions ready to be used, which are widely employed in the pharmaceutical, cosmetic, and veterinary fields, and the property of which is to jell instantaneously when in contact with water and with digestive secretions. They are obtained from a mixture containing:

an oily phase of the type
  mineral oils: paraffin, isoparaffin and cylcoparaffin, etc.
  white mineral oils: isohexadecane, isododecane, etc.
  natural oils: hexamethyltetracosane, squalane, etc.
  synthetic oils: polyisobutene, hydrogenated polyisobutene, etc.
an aqueous phase,
a tensioactive of the type water in oil
a tensioactive of the type oil in water
one or more monomers of the type
  acrylate acrylic acid, metacrylic acid, itaconic acid, maleic acid, etc.

2-hydroxyethylmetacrylate; 2,3-dihydroxypropyl acrylate; 2-hydroxyethyl metacrylate; 2,3-dihydroxypropyl metacrylate, and ethoxylated derivatives, etc.

trimethylolpropane triacrylate, ethylene glycol dimethacrylate, acrylamide, sodium acrylamido-2-methyl-propane-sulphonate, methylenebis (acrylamide), etc.

a complexing agent of the type: diallyloxy acetic acid and salts, triallylamine, diallylurea, etc.

These various mixtures are subjected to a polymerization reaction, followed by a distillation stage.

The preparations thus obtained come under the form of liquids that are more or less viscous, and are able to incorporate active substances, either in the liquid state or in the solid state, as well as excipients modulating the biodisponibility of the preparation obtained in that manner.

The incorporation of such lipophilic or hydrosolube active substances is facilitated by the presence of tensioactives inside those inverted latexes. Such tensioactives also allow us to play on the viscosity of the preparation by the addition of lipophilic or hydrophilic diluting agents.

On the other hand, such preparations are quite suitable for the preparation of sustained release soft capsules or "Licaps®" capsules because of the very little quantity of water in the mixture (distillation). A certain number of patents were issued worldwide concerning these various compositions:

EP0503853, EP1010708, EP1047716, EP1055707, EP1055451, EP1113029, etc.

FR2810883, FR2808447, FR2808446, FR2807046, FR2802936, FR2794124, FR2789395, etc.

WO0135922, WO0032639, etc.

US2001053801.

Some of these products are commercialized under the name "SEPIGEL®" and "SIMULGEL®".

The proportion of these substances that needs to be used in order to obtain the expected matricial effect varies from 0.1% to 100% with respect to the total mass of the excipients.

The lipophilic "hydrocolloide" solutions are liquid preparations containing substances that are polymeric or not, dissolved into a lipophilic phase. Their specificity is, as any hydrocolloide solution, to show some viscosity. But unlike aqueous hydrocolloide solutions that are miscible in water or in hydro-alcoholic solutions, such solutions jell, swell or polymerize when put in contact with water or with digestive secretions. As it was the case hereabove, a matrice is formed at the contact of liquids, a matrice from which the active substances are progressively released. The most interesting thing with such solutions is that they allow to be package in unitary doses. As it was previously the case with the inverted latexes, the presence of water is rather limited in such preparations and such solutions allow the incorporation of an oily phase and of tensioactives in order to facilitate the solubilization and the dispersion of active substances. The substances used for the preparation of such solutions belong to two classes of products:

synthetic polymers, such as copolymers of metacrylic acid ("Eudragit®"), copolymers of acrylic acid ("Carbopol®"), acrylamide polymers, polymers and copolymers of polyethylene oxide, polyamides, polyacrylnitriles, polymers of polyvinyl pyrrolidone, etc.

natural derivatives, such as:

cellulosed derivatives: acetophthalate of cellulose, hydroxypropyl cellulose, ethylcellulose, ethyl hydroxyethyl cellulose, hydroxypropylmethyl phthalate cellulose, cellulose butyrate acetate, cellulose propionate acetate, etc.

starch derivatives, such as modified starches having undergone:

an esterification
an etherification giving birth to derivates of acetic acid, hydroxypropylated derivatives, derivates of succinic acid (octenyl succinate); derivates of glycolic acid, of carboxylic acid, etc.

saccharose (or sucrose) derivatives, such as fatty acid esters: palmitate, stearate, tetrastearate, tristearate, pentastereate, pentalaurate, pentaoleate, tetraoleate, octaoleate pentaurecate, tetraerucate, trirapeate, tetrarapeate, pentarapeate, etc.

derivatives of polyanhydric polyesters, such as polymers of lactic acid and their derivatives, polymers of glycolic acid and their derivatives, the combination of two monomers and their derivatives, etc.

These various compounds are already widely used in the pharmaceutical field for the preparation of sustained release solid matricial intended for oral or subcutaneous administration such as implants. Such forms are obtained either by compression ("Eudragit", ethylcellulose, etc.) or by coating ("Eudragit", cellulose derivatives, starch derivatives, etc.) or by casting or injection molding for the formation of implants, in the case of saccharose derivatives (patents WO0166081, U.S. Pat. No. 6,051,558, YS5968542, U.S. Pat. No. 5,747,058, U.S. Pat. No. 6,291,013, ZUS6045528), of derivatives of lactic acid and glycolic acid (U.S. Pat. No. 4,767,628, U.S. Pat. No. 4,530,840). In all cases, the study of various patents on soft capsules does not mention the use of these components as matricial agent for sustained release forms presented under the form of soft capsules or "Licaps®" hard capsules.

The proportion of these substances to be used in order to obtain the expected matricial effect varies from 0.1% to 90% in weight with respect to the final volume of the lipophilic "hydrocolloide" solution.

In both cases, inverted latexes and lipophilic "hydrocolloide" solutions, the solvents likely to be used for the dilution or dissolution of the matricial agents are extremely varied, having either a lipophilic or hydro-lipophilic nature, allowing thus the incorporation of a great number of active substances in said matrices, whether said active substances are lipophilic, hydrophilic or hydrolipophilic.

The solvents likely to be used for the dilution or the dissolution of said components have a level of toxicity that allows them to be used in the pharmaceutical field. They are:

vegetable oils, hydrogenated vegetable oils, ethoxylated vegetable oils: olive oil, hazelnut oil, coconut oil, castor oil, soybean oil, sesame oil, etc.

mineral oils: paraffin, isoparaffin, cycloparaffin, silicon oils, isohexadecane, isododecane, and derivatives, etc.

natural oils, squalane, hexamethyltetracosane; mono-, di-, and tryglycerides, etc.

synthetic oils: polyisobutene, hydrogenated polyisobutene, etc.

and other solvents: ethanol, propanol-1, propanol-2, polypropylene, polypropylene carbonate, dimethyl isosorbide ether, polyoxyethylene. glycols (Macrogols), glycerol, fatty acid esters of polyethylene, fatty acid esters of propylene glycol, propylene glycol dicaprylate/dicaprate, glycerol caprylate/caprate, fatty acid esters of polyoxyethylene/polyoxypropylene glycol, triacetin, isopropyle myristate, glycofurol, liquid esters of fatty acids, ethyl acetate, butanol, propylene glycol acetate, butyl acetate, ethyleneglycol monobutyl ether, lactate ethyl, butyl acetate, monoethylic ether of diethyleneglycol, glycerin mono-oleate, glycerin linoleate, fatty acid esters and glycerol esters, esters of glycerol fatty acid and PEG esters, etc.

The proportion of these substances to be used in such preparations depends on the solubility of the active substances and may vary from 1% to 80% in mass with respect to the total weight of the excipients.

As it has been shown during a certain number of tests, the various matricial agents mentioned hereabove give birth to a viscous lattice with a soft to hard consistency having a gelatinous aspect or to a solid lattice under poriferous form (aspect of a sponge) with a more or less rigid structure. In both cases, such structures may be reinforced by the introduction into the environment of substances that, when in contact with digestive secretions, will increase the solidity of the viscous or poriferous lattice. We may obtain such result through three different methods:

incorporation of lipophilic "hydrocolloide" solutions into the inverted latexes. As the inverted latex serves as a bonding material (preventing the dispersion of particles into the gastric secretions), we obtain a compact polymeric lattice by precipitation inside of the viscous gangue. Such structure is obtained by the progressive penetration of the digestive secretions inside the viscous lattice. The proportion of lipophilic "hydrocolloide" solutions necessary to obtain such structures may vary from 0.1% to 90% in weight with respect to the mass of the inverted latex that is incorporated inside the final mixture.

incorporation of substances (under the form of hydrophilic additives) that swell when put in contact with water. As they are entrapped inside the inverted latexes or inside the lipophilic "hydrocolloide" solutions, such substances progressively swell and thus slow down in a significant proportion the release of the active substance incorporated in such matrice. The consistency of said matrices is similar to that of gelatine: firm structure. The substances that meet that standard belong to the class of:

celluloses and their derivatives: methyl, hydroxypropyl, hydroxyethyl, hydroxymethyl, hydroxypropylmethyl, carboxymethyl, etc. whether slightly substituted or not, cross-linked or not, and the viscosities of which may vary from 100 cPs to more than 100,000 cPs.

starches and their derivatives: corn, potato, wheat, rice, and tapioca starches whether native or pregelatinated, whether they have been subjected or not to a dextrenization, an acid treatment of whatever strength, an oxidation, a cross-linking in the presence of adipic, acetic, phosphoric acid, an etherification, an enzymatic transformation, etc. or a combination of said chemical reactions hereabove mentioned.

polysaccharides, such as guar, xanthan, tragacanth, and acacia gums, carob, pectins, alginates, carraghenanes, gellan gums, chitosan, etc.

polymers of vinylpyrrolidone and its derivatives. These substances are all the more interesting that their swelling power in water is greatly increased when they are initially moisturized with organic solvents, such as it is the case with hydroxypropyl methyl celluloses, carraghenanes, etc. The proportion that may be introduced inside the environment in order to obtain a release varying from one hour to twenty-four hours is about 0% to 80% in weight with respect to the total mass of the excipients. A important in order to obtain rapidly a structure that is compact, is the size of the particles of said substances. Indeed, the smaller the particles the greater the swelling power, and the lattice formed is much denser (less intersticies between the particles). Thus, the size of the particles that will permit to obtain such a result must be comprised between 1 µm and 1000 µm, with a preference for sizes comprised between 1 µm and 100 µm.

incorporation of plasticizers. The goal of such substances is to provide for a certain elasticity to the matrice of poriferous nature, so that the negative effects of the intestinal peristalsis on a rigid structure may be countered. Among the various substances used as plasticizers, we have selected triacetin, dibutyl phthalate, diethylphthalate, dibutyl sebacate and saccharose isosorbate acetate. The proportion of plasticizers that may be introduced into preparations of the lipophilic "hydrocolloide" solution type is comprised between 0 and 80%.

The active substances that may be used for such processing belong to all pharmacological categories, that is: antalgics, antiinflammatories, antispasmodics, cytotoxics, cardiovascular products (hypertensors, hypotensors, antiarythmics, etc.), antibiotics, antifongics, antiseptics, antiparasitics, hormones, antiviral medications, antiepileptics, antiparkinsonians, antimysasthenics, migraine medications, antivertigo medications, antiallergics, antitussives, bronchial fluidifiers, respiratory analeptics, neuroleptics, anxiolytics, hypnotics, antidepressors, normothymics, psychostimulants, sedatives, myorelaxants, diuretics, etc.

Various examples are given hereafter showing the various possibilities that are available in order to obtain sustained release encapsulated matricial.

Such active substances may be incorporated:

under liquid form: hydrolipophilic solutions, emulsions, self-dispersing micro-emulsions, etc.

under solid form in the state of:

powders with a granulometric distribution with sizes ranging from 1 micron to 1000 µm micro-granules or pellets coated or not with a granulometry of 10 µm to 1000 µm.

absorbats: liquid products fixed on a neutral support in order to increase the stability of the active substance, the granulometry of such supports varies from the micron to 1000 µm.

The different solvents that may be used in order to solubilize or disperse these various active substances are identical to those previously described for the dilution of the inverted latexes or for the preparation of the lipophilic "hydrocolloide" solutions.

We may add to these various solvents some tensioactives facilitating the dispersion or the solubilization of the active substances. The tensioactives that may be used in this invention are as follows:

non ionic tensioactives:

sorbitane esters: polysorbates, spans, tweens, etc.

polyethoxylated fatty acids: PEG 8 stearate to PEG 100 stearate;

polyethoxylated fatty alcohols: mixture of monolaurate ether having a PEG containing 4 to 23 oxyethylenated groups on the polyoxyethylenic chain, etc.

glycol esters: methylglycol stearate;

glycerol esters: glycerol monostearate, PEG 75 stearate, glycol stearate with a PEG comprised between 6 and 32, etc.

PEG esters;

saccharose esters;

fatty alcohol and PEG ethers: Brij;

alkyl phenol and PEG ethers;

tensioactives with an amide function:

monoethanolamide of copra fatty acid, of lauric acid, etc.

diethanolamide of myristic acid, of lauric acid, et.

mono-isopropanolamine of lauric acid.

lecithines ionic tensioactives:

sulphated derivatives: sodium laurylsulphate and its derivatives;

sulphonated derivatives: sodium dodecylsulphosuccinate and its derivatives;

quaternary ammoniums: cetyltrimethylammonium chloride, lauryl pyridinium, distearyl dimethyl ammonium, etc.

amphoterics: copra alkyl dimethyl ammonium betaine, derivatives of fatty acid amines with betainic structure, lauryl-α-iminodipropionic acid and its derivatives, lauryl-α-myristyl-α-aminopropionic acid and its derivatives, etc.

The quantity of these substances used to facilitate the solubilization or dispersion of active substances may vary from 0 to 50% in weight with respect to the total mass of the excipients.

According to the type of matrice obtained at the contact of digestive secretions, we may incorporate dissolution accelerators into the final mixture. Because of their rapid dissolution when in contact with the digestive secretions, such substances are aimed at creating a porous lattice if the one obtained with the matricial system is too compact. Such substances are put in suspension in the lipophilic environment. They are:

lactose,
mono and basic phosphates (calcium, sodium, potassium)
polyols: sorbitol, maltodextrines, dextrose, maltitol, xylitol, maltisorb, manitol, etc.

Such substances are used at a concentration that may vary from 0 to 50% in weight with respect to the total mass of the excipients.

In some cases, we may find it necessary to employ buffer systems in order to maintain the active substances in suspension or to allow the solubilization of said substances, and even in order to increase the intrinsic viscosity of the matrice, if the latex is sensitive to the influence of the pH of the environment of the dissolution. The components that allow to reach such goals are acids and bases as well as their corresponding salts. Therefore, we may use:

citric acid and sodic, potassic and calcic salts
phosphoric acid (ortho and meta) and sodium, potassium, and calcium salts, mono and dibasic
sodium, potassium, and calcium carbonates
phthalic acid and sodium, potassium, and calcium salts
hydrochloric acid and sodium, potassium, and calcium salts
boric acid and sodium, potassium, and calcium salts
acetic acid and sodium, potassium, and calcium salts
lactic acid and sodium, potassium, and calcium salts
propionic acid and sodium, potassium, and calcium salts
sodium, potassium, and calcium hydroxides.

The proportion of these various additives, used alone or combined and varying according to the expected goal, varies from 0% to 50% in weight with respect to the total mass of the excipients. Such substances may be introduced in the dissolved or solid state inside the preparation. In the solid state, these different components form an intra-matricial micro environment, which may be basic or acid, during their progressive solubilization, allowing thus to modulate the release of the substance from such system.

The solutions or suspensions thus prepared, giving birth in situ to sustained release matricial, show viscosities ranging from 50 millipascals to 500,000 millipascals.

Such solutions or suspensions are conditioned in soft capsules or in hard capsules of the "Licaps®" type.

The wall of these hard capsules or soft capsules may be composed of gelatine but also of carraghenanes, starches or of cellulose hydroxypropylmethylcellulose.

After the opening or the dissolution of the tunic, such systems allow the active substance to be released progressively through a period ranging form one hour to twenty-four hours, this release kinetics being slightly or not dependent of the surrounding biological factors. The order of the dissolution kinetics, which may be dependent or not of the pH, may be zero or one, according to the type of excipients used in order to obtain such release.

The invention is not limited in its application as the active substances may belong to all therapeutical classes.

This invention also deals with the manufacturing method of said compositions by means of a simple mixture of the various components, performed with or without heat, followed by a conditioning under the form of soft capsules or hard capsules. Performed with or without heat depending on the components of the formula to be prepared, the manufacturing is divided into two or three principal stages depending on the matricial agent used. Examples of preparations, which are described hereafter, are composition formulas that may be obtained with this invention, but they do not limit the latter in any way.

Example 1

Ibuprofen

Sustained Release Soft Capsules

Ibuprofen* . . . 200.0000 g
Inverted latex ("Sepigel 305®") QS . . . 600.0000 g

In a two-liter beaker, introduce "Sepigel 305®". Add ibuprofen. Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2 (see FIG. 1).

Ibuprofen ("Basf") used shows an average granulometry of 25 μm.

Example 2

Ibuprofen

Sustained Release Soft Capsules

Figure 2:
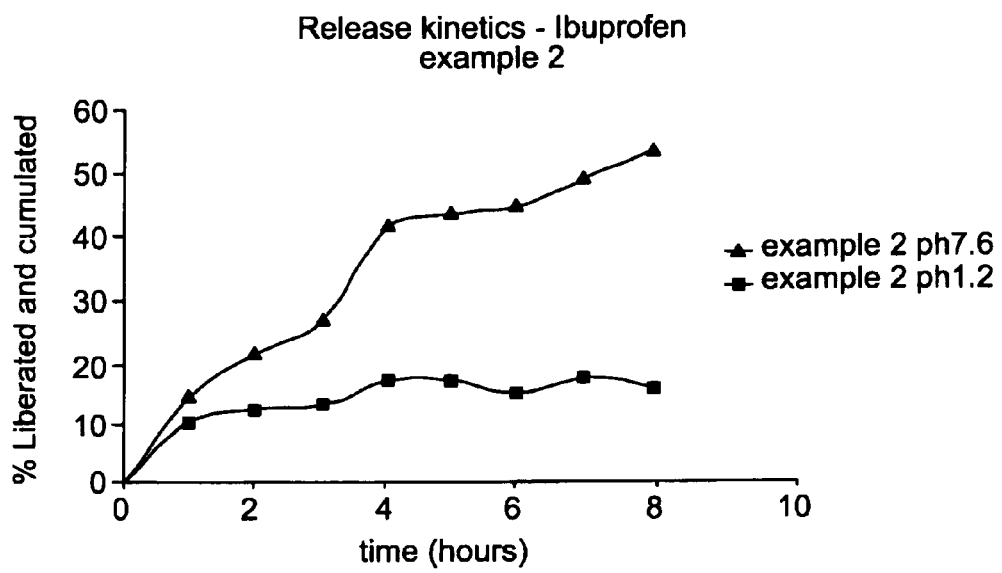
FIG. 2 is a graph of Example 2.

Ibuprofen . . . 200.0000 g
Hydroxypropyl starch . . . 200.0000 g
Inverted latex ("Sepigel 305®") QS . . . 600.0000 g Mix thoroughly ibuprofen with hydroxypropyl starch. In a two-liter beaker, introduce "Sepigel 305®". Add the mixture ibuprofen/hydroxypropyl starch. Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2 (see FIG. 2).

Example 3

Ibuprofen

Sustained Release Soft Capsules

Figure 3:
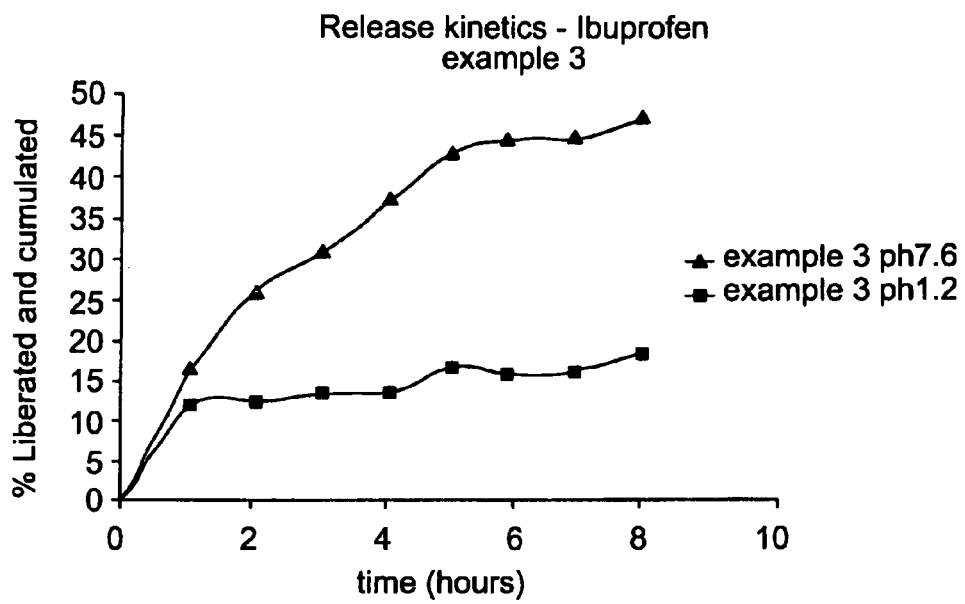
FIG. 3 is a graph of Example 3.

Ibuprofen . . . 200.0000 g
"Montane 20®" . . . 400.0000 g
Inverted latex ("Sepigel 305®") QS . . . 1100.0000 g Heat the mixture ibuprofen/"Montane 20®" at a 40 degree temperature. In a two-liter beaker, introduce "Sepigel 305®". Add the mixture ibuprofen/"Montane 20®". Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2 (see FIG. 3).

Example 4

Ibuprofen

Sustained Release Soft

Figure 4:
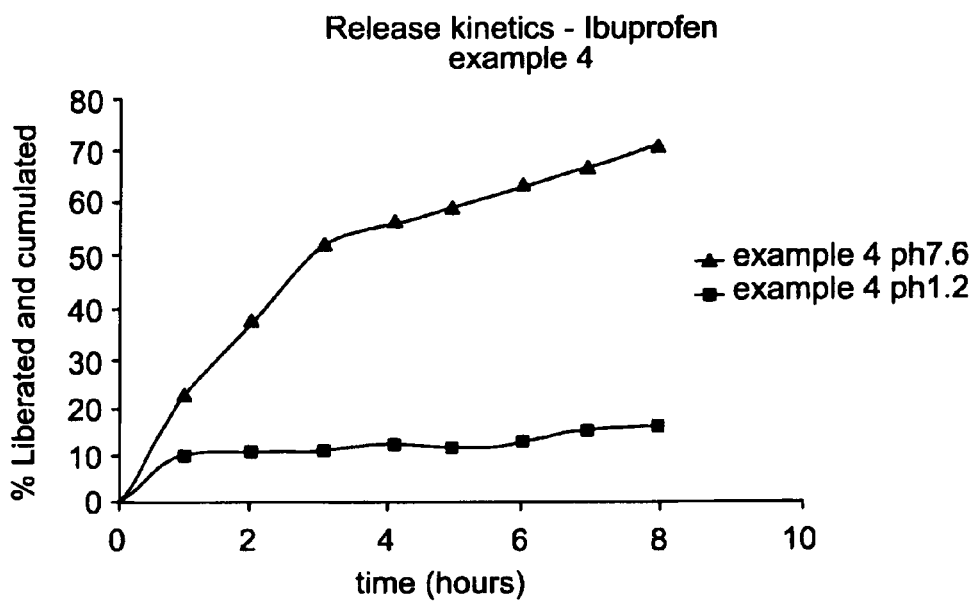
FIG. 4 is a graph of Example 4.

Ibuprofen . . . 200.0000 g
Glycerine mono-oleate . . . 400.0000 g
Inverted latex ("Sepigel 305®") QS . . . 1100.0000 g Heat the mixture ibuprofen/glycerine mono-oleate at a 40 degree temperature. In a two-liter beaker, introduce "Sepigel 305®". Add the mixture ibuprofen/glycerine mono-oleate. Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2 (see FIG. 4.).

Example 5

Ibuprofen

Sustained Release Soft Capsules

Ibuprofen* . . . 200.0000 g
Potassium phosphate monobasic . . . 6.8050 g
Sodium hydroxide . . . 0.0848 g
Inverted latex ("Sepigel 305®") QS . . . 1000.0000 g In a two-liter beaker, introduce "Sepigel 305®". Add ibuprofen, sodium hydroxide and potassium phosphate monobasic. Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2.

Ibuprofen ("Basf") used shows an average granulometry of 25 p.m.

Example 6

Ibuprofen

Sustained Release Soft Capsules

Ibuprofen . . . 200.0000 g
Monosodic phosphate . . . 1.3000 g
Disodic phosphate . . . 24.4000 g
Inverted latex ("Sepigel 305®") QS . . . 1000.0000 g In a two-liter beaker, introduce "Sepigel 305®". Add ibuprofen, monosodic phosphate and disodic phosphate. Homogenize for 30 minutes until you obtain an homogeneous mixture. Fill elongated soft capsules 8. The study of the dissolution kinetics at pH 7.6 is showing that the release of the substance exceeds 8 hours and 2 hours with a pH of 1.2.

Example 7

Paracetamol

Sustained Release Soft Capsules

Paracetamol . . . 100.0000 g
Glycerine linoleate* . . . 600.0000 g
Neutral copolymer of metacrylic acid** . . . 200.0000 g Dissolve at 100° C. the neutral copolymer of the metacrylic acid into the glycerine linoleate. Cool the mixture down to 30° C.-35° C. and add paracetamol. Homogenize for 30 minutes. Fill elongated soft capsules 8. The study of the dissolution kinetics at pH 7.6 is showing that the release of the substance exceeds 6 hours.

*: "Maisine®: Gattefossé"
**: "Plastoid B®: Röhm Pharma"

Example 8

Paracetamol

Sustained Release Soft Capsules

Paracetamol . . . 100.0000 g
Glycerine linoleate* . . . 700.0000 g
Lactose . . . 100.0000 g
Neutral copolymer of metacrylic acid** . . . 100.0000 g Dissolve at 100° C. the neutral copolymer of the metacrylic acid into the glycerine linoleate. Cool the mixture down to 30° C.-35° C. and add paracetamol and lactose. Homogenize for 30 minutes. Fill elongated soft capsules 8. The study of the dissolution kinetics at pH 7.6 is showing that the release of the substance exceeds 4 hours.

*: "Maisine®: Gattefossé"
**: "Plastoid B®: Röhm Pharma"

Example 9

Paracetamol

Sustained Release Soft Capsules

Paracetamol . . . 100.0000 g
Glycerine linoleate* . . . 450.0000 g
Neutral copolymer of metacrylic acid** . . . 100.0000 g
"Sepigel 305®"*** . . . 350.0000 g Dissolve at 100° C. the neutral copolymer of the metacrylic acid into the glycerine linoleate. Cool the mixture down to 30° C.-35° C. and add paracetamol. Homogenize. Add Sepigel 305®. Homogenize for 30 minutes. Fill elongated soft capsules 8. The study of the dissolution kinetics at pH 7.6 is showing that the release of the substance exceeds 8 hours and 2 hours with a pH of 1.2.

*: "Maisine®: Gattefossé"
**: "Plastoid B®: Röhm Pharma"
***: "Sepigel 305®: Seppic"

Example 10

Diclofenac

Sustained Release Soft Capsules

Diclofenac . . . 25.0000 g
Monoethylic ether of diethylene glycol* . . . 450.0000 g
Hydroxypropylcellulose slightly substituted** . . . 25.0000 g Dissolve at 70° C. the slightly substituted hydroxypropylcellulose into the monoethylic ether of diethyleneglycol. Cool the mixture down to 25° C. and add diclofenac. Homogenize for 30 minutes. Fill elongated soft capsules 4. The study of the dissolution kinetics at pH 7.6 is showing that the release of the substance exceeds 5 hours.

*: "Transcutol P®: Gattefossé"
**: "HP 55®: Seppic"

Example 11

Diclofenac

Sustained Release Soft Capsules

Diclofenac . . . 25.0000 g
Monoethylic ether of diethylene glycol* . . . 450.0000 g
Sesame oil . . . 225.0000 g
Hydroxypropylcellulose slightly substituted** . . . 25.0000 g Dissolve at 90° C. the slightly substituted hydroxypropylcellulose into the monoethylic ether of diethyleneglycol. Cool the mixture down to 25° C. and add sesame oil and diclofenac. Homogenize for 30 minutes. Fill elongated soft capsules 4. The study of the dissolution kinetics at pH 7.6 is showing that the release of the substance exceeds 6 hours.

*: "Transcutol P®: Gattefossé"
**: "HP 55®: Röhm Pharma"

Example 12

Diclofenac

Sustained Release Soft Capsules

Diclofenac . . . 25.0000 g
Monoethylic ether of diethylene glycol* . . . 450.0000 g
Hydroxypropylcellulose slightly substituted** . . . 25.0000 g
"Sepigel 305®"*** . . . 50.0000 g Dissolve at 70° C. the slightly substituted hydroxypropylcellulose into the monoethylic ether of diethyleneglycol. Cool the mixture down to 25° C. and add diclofenac. Homogenize. Add Sepigel 305®. Homogenize for 30 minutes. Fill elongated soft capsules 4. The study of the dissolution kinetics at pH 7.6 is showing that the release of the substance exceeds 8 hours and 2 hours with a pH of 1.2.

*: "Transcutol P®: Gattefossé"
**: "HP 55®: Seppic"
***: "Sepigel 305®: Seppic"

Example 13

Dimenhydrinate

Sustained Release Soft Capsules

Dimenhydrinate . . . 50.0000 g
Monoethylic ether of diethylene glycol* . . . 225.0000 g
Cellulose acetate butyrate . . . 225.0000 g Dissolve the cellulose acetate butyrate into the monoethylic ether of diethyleneglycol. Add the dimenhydrinate. Homogenize for 30 minutes. Fill elongated soft capsules 4. The study of the dissolution kinetics at pH 7.6 is showing that the release of the substance exceeds 4 hours.

*: "Transcutol P®: Gattefossé"

Example 14

Dimenhydrinate

Sustained Release Soft Capsules

Dimenhydrinate . . . 50.0000 g
Monoethylic ether of diethylene glycol* . . . 22.0000 g
Cellulose acetate butyrate . . . 200.0000 g
Sucrose acetate butyrate . . . 25.0000 g Dissolve the sucrose acetate butyrate and the cellulose acetate butyrate into the monoethylic ether of diethyleneglycol. Add the dimenhydrinate. Homogenize for 30 minutes. Fill elongated soft capsules 4. The study of the dissolution kinetics at pH 7.6 is showing that the release of the substance exceeds 6 hours.

*: "Transcutol Gattefossé"

Example 15

Dimenhydrinate

Sustained Release Soft Capsules

Dimenhydrinate . . . 50.0000 g
Monoethylic ether of diethylene glycol* . . . 425.0000 g
"Sepigel 305®" . . . 400.0000 g
Sucrose acetate butyrate . . . 25.0000 g Dissolve the sucrose acetate butyrate into the monoethylic ether of diethyleneglycol. Add the dimenhydrinate. Homogenize for 10 minutes. Add the hydroxypropyl starch. Homogenize for 10 minutes. Add "Sepigel 305®". Homogenize for 30 minutes. Fill elongated soft capsules 8. The study of the dissolution kinetics at pH 7.6 is showing that the release of the substance exceeds 8 hours.

*: "Transcutol P®: Gattefossé"

The invention claimed is:

1. Sustained release viscous liquid compositions for capsules, the compositions comprising:
   (i) at least one liquid matrix ingredient of the inverted latex class, the at least one liquid matrix ingredient creating in situ a biodegradable matrix, more or less compact, due to an instantaneous physical modification of the capsule content immediately after the dissolution of the shell of the capsule;
   (ii) at least one active ingredient;
   (iii) at least one solvent for active ingredient solubilization or dispersion; and
   (iv) at least one ingredient modulating the release of the active ingredient from the matrix formed in situ for more than one hour after dissolution of the shell of the capsule.

2. Sustained release viscous liquid compositions for capsules according to claim 1, wherein the instantaneous physical modification of the capsule content is obtained from the inverted latexes.

3. Sustained release viscous liquid compositions for capsules according to claim 1, wherein the instantaneous physical modification of the capsule content is a jellification or reticulation of the liquid matrix ingredient under digestive secretion contact.

4. Sustained release viscous liquid compositions for capsules according to claim 1, wherein the instantaneous physical modification of the capsule content occurs between 1 second and 10 minutes after opening of the capsule.

5. Sustained release viscous liquid compositions for capsules according to claim 1, wherein the inverted latexes are derivatives of acrylic acid or of acrylamide polymers.

6. Sustained release viscous liquid compositions for capsules according to claim 1, wherein the at least one liquid matrix ingredient represents 0.1 to 100% of the total mass of the ingredients.

7. Sustained release viscous liquid compositions for capsules according to claim 1, wherein the viscosity of the liquid composition is between 50 millipascals and 500,000 millipascals.

8. Sustained release viscous liquid compositions for capsules according to claim 1, wherein the active ingredients belong to therapeutic classes.

9. Sustained release viscous liquid compositions for capsules according to claim 1, wherein the active ingredient is in the liquid state or dispersed in the solvent.

10. Sustained release viscous liquid compositions for capsules according to claim 1, wherein the active ingredient is dissolved or dispersed in oils or organic solvents having a lipophilic, hydrophilic or hydrolipophilic nature.

11. Sustained release viscous liquid compositions for capsules according to claim 1, wherein the active ingredient is in the solid state and dispersed in uncoated powder form, coated powder form, or an absorbent.

12. Sustained release viscous liquid compositions for capsules according to claim 11, wherein the active ingredient in the solid state has a granulometry between 1 µm to 100 µm.

13. Sustained release viscous liquid compositions for capsules according to claim 1, wherein the ingredient modulating the release kinetics of the active ingredient is selected from the group consisting of hydrophilic additives, plasticizers, tensioactives, dissolution accelerators class and buffer systems.

14. Sustained release viscous liquid compositions for capsules according to claim 13, wherein the ingredient modulating the release kinetics of the active ingredient is a hydrophilic additive is selected from the group consisting of cellulose and cellulose derivatives, starches and their derivatives, polysaccharides, and polymers of vinylpyrrolidone.

15. Sustained release viscous liquid compositions for capsules according to claim 13, wherein the ingredient modulating the release kinetics of the active ingredient is a hydrophilic additive having a concentration between 0% and 80% by weight with respect to the total mass of the ingredients.

16. Sustained release viscous liquid compositions for capsules according to claim 13, wherein the ingredient modulating the release kinetics of the active ingredient is a hydrophilic additive having a granulometry between 1 µm and 1000 µm.

17. Sustained release viscous liquid compositions for capsules according to claim 1, wherein the release of the active ingredient from such matrices varies from one hour to twenty-four hours.

18. Sustained release viscous liquid compositions for capsules according to claim 1, wherein the composition is conditioned in a hard or a soft capsule.

19. Sustained release viscous liquid compositions for capsules according to claim 1, wherein the composition of the capsule shell is selected from the group consisting of gelatin, starches, hydroxypropylmethylcellulose, carrageenan and polyvinylic alcohol polymers.

20. Sustained release viscous liquid compositions for capsules according to claim 1, wherein the concentration of solid material in the liquid matrix ingredients is between 0.1% and 90% by weight to the volume of the liquid matrix ingredients.

21. Sustained release viscous liquid compositions for capsules according to claim 1, wherein the invert latexes are liquid polymers coming from the polymerization of a liquid medium containing an acrylate or acrylamide monomer, an oily phase, an aqueous phase, a tensioactive of the type water-in-oil, a tensioactive of the type oil-in-water, and a complexing agent.

* * * * *

UNITED STATES PATENT AND TRADEMARK OFFICE
CERTIFICATE OF CORRECTION

PATENT NO. : 8,734,839 B2  
APPLICATION NO. : 10/511260  
DATED : May 27, 2014  
INVENTOR(S) : Laurence Paris It is certified that error appears in the above-identified patent and that said Letters Patent is hereby corrected as shown below:

In the Specification

Column 2, Line 38 insert --be-- after the word "may"

Column 2, Line 45 delete "57,776,482" insert --5,776,482--

Column 3, Line 21 after the word "soft" insert --capsules--

Column 5, Line 52 delete "package" insert --packaged--

Column 6, Line 7, 8 and 9 delete the word "derivates" insert --derivatives--

Column 6, Line 28 delete "Z"

Column 7, Line 80 delete "A"

Column 8, Line 62 delete "et." insert --etc.--

Column 9, Line 67 delete "form" insert --from--

Column 11, Line 9 insert --capsules-- after the word "soft"

Column 11, Line 40 delete "p.m." insert --um--

Signed and Sealed this  
Eighteenth Day of November, 2014

Michelle K. Lee  
*Deputy Director of the United States Patent and Trademark Office*